United States Patent [19]

Kella

[11] 3,938,389
[45] Feb. 17, 1976

[54] HAND AND ARM STRENGTH MEASURING DEVICE

[75] Inventor: Harry Y. Kella, San Diego, Calif.

[73] Assignee: The Raymond Lee Organization, Inc., New York, N.Y. ; a part interest

[22] Filed: Feb. 27, 1975

[21] Appl. No.: 553,563

[52] U.S. Cl. .................. 73/381; 272/67; 272/83 A
[51] Int. Cl.² ............................................ G01L 5/06
[58] Field of Search.................... 73/379, 380, 381; 272/83 R, 83 A, 67, DIG. 5

[56] References Cited
UNITED STATES PATENTS

| 468,154 | 2/1892 | McClure | 73/380 |
| 496,094 | 4/1893 | Perloquin | 73/381 |
| 911,925 | 2/1909 | Zeno | 73/381 |

FOREIGN PATENTS OR APPLICATIONS

| 246,677 | 4/1926 | Italy | 73/380 |
| 1,387,117 | 12/1964 | France | 73/380 |

*Primary Examiner*—Jerry W. Myracle
*Assistant Examiner*—John P. Beauchamp
*Attorney, Agent, or Firm*—Daniel Jay Tick

[57] ABSTRACT

A helical spring has one end extending at right angles to the axis of the spring and affixed to a support platform and another end extending at right angles to the axis and at right angles to the one end and perpendicularly to the plane of the platform. A handle is provided at the other end of the spring. A meter device is coupled to the spring at the other end thereof in a manner whereby when the handle is gripped manually and moved in a direction about the axis of the spring in a plane perpendicular to the axis the meter device indicates the force applied to the handle and therefore measures the strength of the hand and arm applying the force.

2 Claims, 3 Drawing Figures

HAND AND ARM STRENGTH MEASURING DEVICE

DESCRIPTION OF THE INVENTION

The present invention relates to a hand and arm strength measuring device.

Objects of the invention are to provide a hand and arm strength measuring device of simple structure, which is inexpensive in manufacture, and functions efficiently, effectively and reliably to measure the strength of the hand and arm of a user.

In order that the invention may be readily carried into effect, it will now be described with reference to the accompanying drawing, wherein.

In the FIGS., the same components are identified by the same reference numerals.

Figure 1:
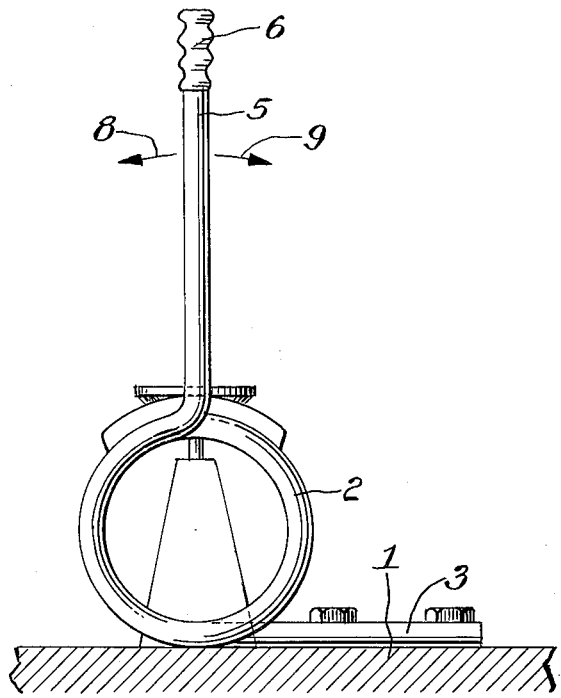
FIG. 1 is an axial view of an embodiment of the hand and arm strength measuring device of the invention.

The hand and arm strength measuring device of the invention comprises a support platform 1.

A substantially helical spring 2 has one end 3 extending at substantially right angles to the axis 4 (FIG. 2) of the spring and affixed to the platform 1. The spring 2 has another end 5 (FIGS. 1 and 2) extending at substantially right angles to the axis 4 and substantially perpendicularly to the plane of the platform 1.

A handle 6 (FIGS. 1 and 2) is provided at the other end 5 of the spring 2.

Figure 2:
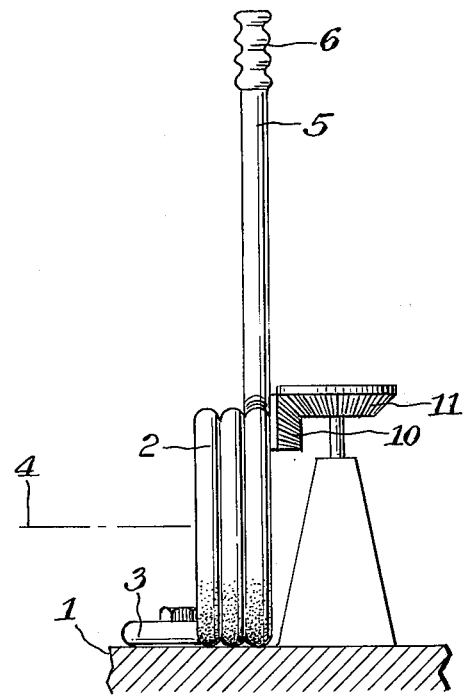
FIG. 2 is a side view of the embodiment of FIG. 1.
Figure 3:
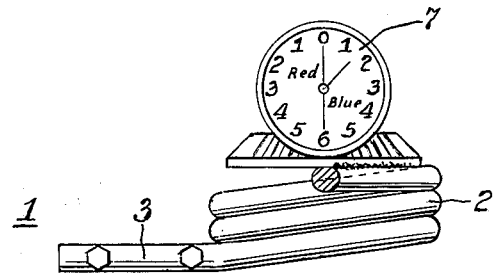
FIG. 3 is a top view of the embodiment of FIG. 1.

A meter device 7 (FIG. 3) is coupled to the spring 2 at the other end 5 thereof in a manner whereby when the handle 6 is gripped manually and moved in a direction, indicated by arrows 8 and 9 in FIG. 1, about the axis 4 of the spring in a plane substantially perpendicular to said axis, the meter device indicates the force applied to the handle and therefore measures the strength of the hand and arm applying the force.

The meter device 7 may comprise any suitable known meter device for indicating force and is coupled to the spring 2 by any suitable gear coupling arrangement such as, for example, worm gears 10 and 11 (FIG. 2), in a manner whereby the meter device measures the resistance of the spring to the force applied thereto, thereby measuring such force.

While the invention has been described by means of a specific example and in a specific embodiment, I do not wish to be limited thereto, for obvious modifications will occur to those skilled in the art without departing from the spirit and scope of the invention.

I claim:

1. A hand and arm strength measuring device, comprising
    a support platform;
    a substantially helical spring having one end extending at substantially right angles to the axis of the spring and affixed to the platform and another end extending at substantially right angles to the axis and at substantially right angles to the one end and substantially perpendicularly to the plane of the platform;
    a handle at the other end of the spring; and
    meter means coupled to the spring at the other end thereof in a manner whereby when the handle is gripped manually and moved in a direction about the axis of the spring in a plane substantially perpendicular to said axis the meter means indicates the force applied to the handle and therefore measures the strength of the hand and arm applying the force.

2. A hand and arm strength measuring device as claimed in claim 1, further comprising gear coupling means coupling the meter means to the spring.

* * * * *